(12) United States Patent
Qian et al.

(10) Patent No.: US 7,598,487 B2
(45) Date of Patent: Oct. 6, 2009

(54) MICRO-HYDROCARBON ANALYSIS

(75) Inventors: Kuangnan Qian, Belle Mead, NJ (US); William N. Olmstead, Basking Ridge, NJ (US); Jason B. English, Roswell, NM (US); Larry A. Green, Mickleton, NJ (US); Roland B. Saeger, Runnemede, NJ (US); Stephen B. Jaffe, Moorestown, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 389 days.

(21) Appl. No.: 11/598,873

(22) Filed: Nov. 14, 2006

(65) Prior Publication Data

US 2007/0114377 A1    May 24, 2007

Related U.S. Application Data

(60) Provisional application No. 60/738,749, filed on Nov. 22, 2005.

(51) Int. Cl.
*G01N 30/02* (2006.01)
*G01N 31/00* (2006.01)

(52) U.S. Cl. .................. 250/282; 702/22; 73/23.35

(58) Field of Classification Search .................. None
See application file for complete search history.

(56) References Cited

U.S. PATENT DOCUMENTS

| | | | |
|---|---|---|---|
| 5,076,909 A | 12/1991 | Overfield et al. | |
| 5,144,127 A | 9/1992 | Williams et al. | |
| 5,774,381 A | 6/1998 | Mcicr | |
| 5,808,180 A * | 9/1998 | Roussis et al. | 73/23.35 |
| 6,952,945 B2 | 10/2005 | O'Brien | |
| 2005/0150815 A1 | 7/2005 | Johnson et al. | |

* cited by examiner

*Primary Examiner*—David A Vanore
(74) *Attorney, Agent, or Firm*—Paul E. Purwin

(57) ABSTRACT

The present invention is a method to determine the composition of a hydrocarbon feedstream from a small sample of hydrocarbons including the steps analyzing the sample with a combination of chromatograph and mass spectrometer, and reconciling output from step a) with other analytical measurements to determine to determine the composition of the hydrocarbon feedstream.

24 Claims, 14 Drawing Sheets

Micro-Hydrocarbon Analysis Protocol

Micro-Hydrocarbon Analysis Protocol

Analysis of an n-paraffin mixture showed that GC-FI-TOF MS can detect molecules boiling from 98°C to 545°C. Only molecule ion and corresponding 13C isotope were generated for each neutral molecule.

The combination of GC and MS separation resolves about 1500 molecules in a FCC total liquid product

Homologous Series Cores Found in Petroleum

Figure 7
Sample Homologous Series
| Benzenes (X=-6) | | | Naphthalenes (X=2) | | | Fluorenes (X=-2) | | | Dibenzothiophenes (X=2) | | |
|---|---|---|---|---|---|---|---|---|---|---|---|
| | alkyl carbons | MW | | alkyl carbons | MW | | alkyl carbons | MW | | alkyl carbons | MW |
| | 0 | 78 | | 0 | 128 | | 0 | 166 | | 0 | 184 |
| | 1 | 92 | | 1 | 142 | | 1 | 180 | | 1 | 198 |
| | 2 | 106 | | 2 | 156 | | 2 | 194 | | 2 | 212 |
| | 3 | 120 | | 3 | 170 | | 3 | 208 | | 3 | 226 |
| | 4 | 134 | | 4 | 184 | | 4 | 222 | | 4 | 240 |
| | 5 | 148 | | 5 | 198 | | 5 | 236 | | 5 | 254 |
| | 6 | 162 | | 6 | 212 | | 6 | 250 | | 6 | 268 |
| | 7 | 176 | | 7 | 226 | | 7 | 264 | | 7 | 282 |
Figure 8
Saturate Cores
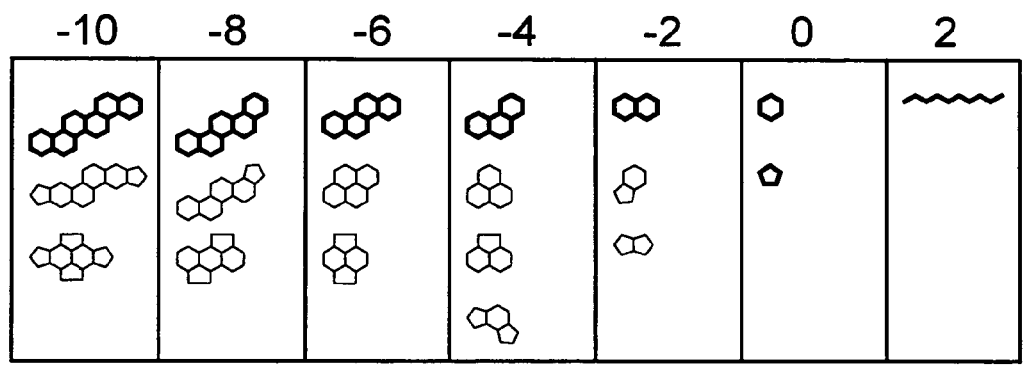
Figure 9
1-Ring Aromatic Cores
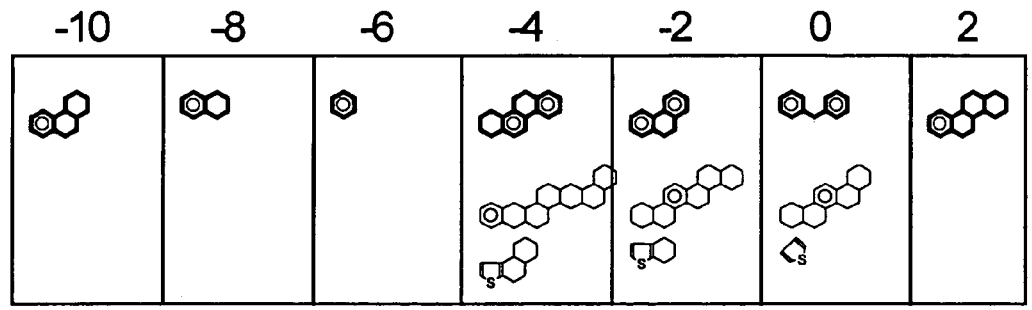

2-Ring Aromatic Cores

3-Ring Aromatic Cores

4-Ring Plus Aromatic Cores

Sulfide Cores

Polar Cores

Olefin and Thiophene Cores

Boiling Point Distribution

Cumulative Distributions Wt vs Wp

Factor vs Boiling Point

Iterative Model-of-Composition Synthesis Algorithm

MICRO-HYDROCARBON ANALYSIS

This application claims the benefit of U.S. Provisional application 60/738,749 filed Nov. 22, 2005.

BACKGROUND OF THE INVENTION

The present invention is a method for analyzing a small hydrocarbon sample to determine the composition of the sample. In particular, the sample is analyzed by a gas chromatograph and field ionization time of flight mass spectrometer.

Petroleum samples are complicated hydrocarbon mixtures containing paraffins, cyclic paraffins, multiring aromatics, and various heteroatomic hydrocarbons (most commonly O, S, and N). Virgin petroleum crude oils contain molecules of a wide boiling point range from highly volatile $C_4$ hydrocarbons to nonvolatile asphaltenes. Analysis of petroleum composition of various boiling ranges is necessary for inputs to many subsequent processes.

SUMMARY OF THE INVENTION

The present invention is a method to determine the composition of a hydrocarbon sample. The method includes the steps of analyzing the sample with a combination of chromatograph and mass spectrometer, and reconciling the output with other analytical measurements to generate a self-consistent model of composition of the said hydrocarbon sample.

In a preferred embodiment, the combination of the chromatograph and mass spectrometer is a gas chromatograph field ionization time-of-flight mass spectrometer (GC-FI-TOF-MS). The data from the mass spectrometer is then reconciled with other analytical measurements, such as those from super critical fluid chromatography (SFC), sulfur simulated distillation (SIMDIS), simulated distillation (S-SIMDIS), N and S elemental analysis, $^1$H-NMR and GC-Flame Ionization Detection (FID) for normal paraffins. The reconciled data gives a detailed identification and quantification of petroleum compositions (referred to micro-hydrocarbon analysis, MHA) which are used as input for modeling of petroleum refinery processes.

BRIEF DESCRIPTION OF THE DRAWINGS

FIG. 7 shows sample homologous series of benzene, naphthalene, fluorine, and dibenzothiophene.

FIG. 8 shows sample saturates arranged by x-class. Reading from right to left the molecules are O ring saturates, 1 ring saturates, 2 ring saturates etc.

FIG. 9 shows 1 ring aromatic cores arranged by x-class, preferred structures in bold.

as a function of boiling point.

Figure 17:
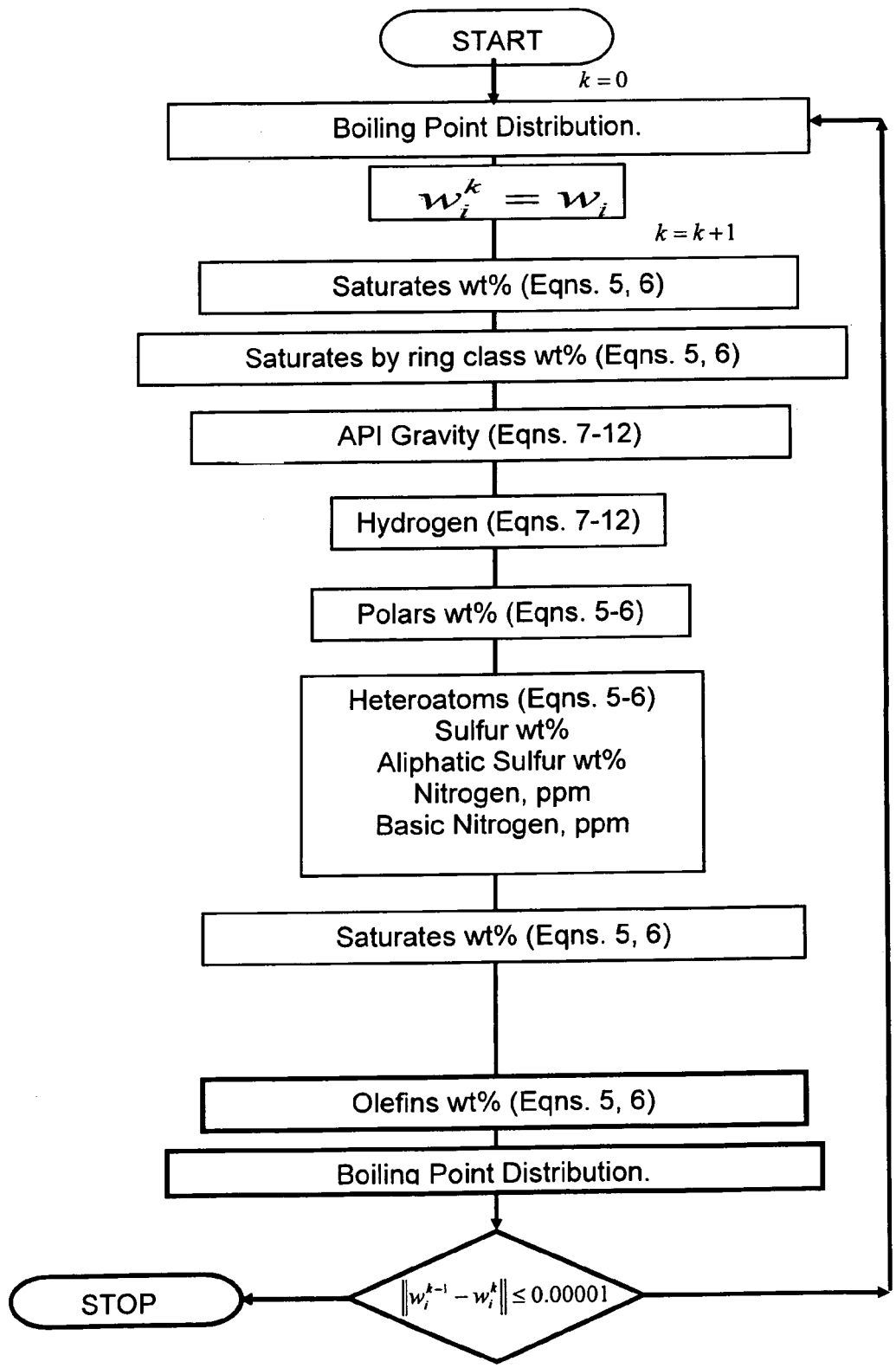

FIG. 17 shows a flow chart for the successive substitution reconciliation algorithm of the present invention.

DETAILED DESCRIPTION OF THE PREFERRED EMBODIMENTS

Molecule Management has become increasingly important in petroleum research, refinery processing, and raw materials evaluation. Molecular compositions of crude oils and intermediate refinery streams are key input parameters to Structure Oriented Lumping (SOL) process models, Optimizable Refinery Models (ORM's) and Real Time Optimization (RTO) Models. In addition to guiding commercial selection of crude oils and refinery processing conditions, these models have become useful for both guidance and development of R&D programs. Molecular composition has become the basis for developing the current process models and evaluating the economic value of crude oils. The current art of obtaining petroleum composition involves various stages of distillation and fractionation followed by detailed analysis. Unfortunately, small sample size and need for quick results can be a significant barrier for applying the current state of the art analysis. For example, Advanced Catalyst Evaluation (ACE) pilot units used in catalytic cracking research routinely generate less than 1 gram of total liquid product (TLP). Even when sufficient volume of sample is available for the traditional characterization, it is a time-consuming process that limits the rate at which samples can be analyzed.

Figure 1:
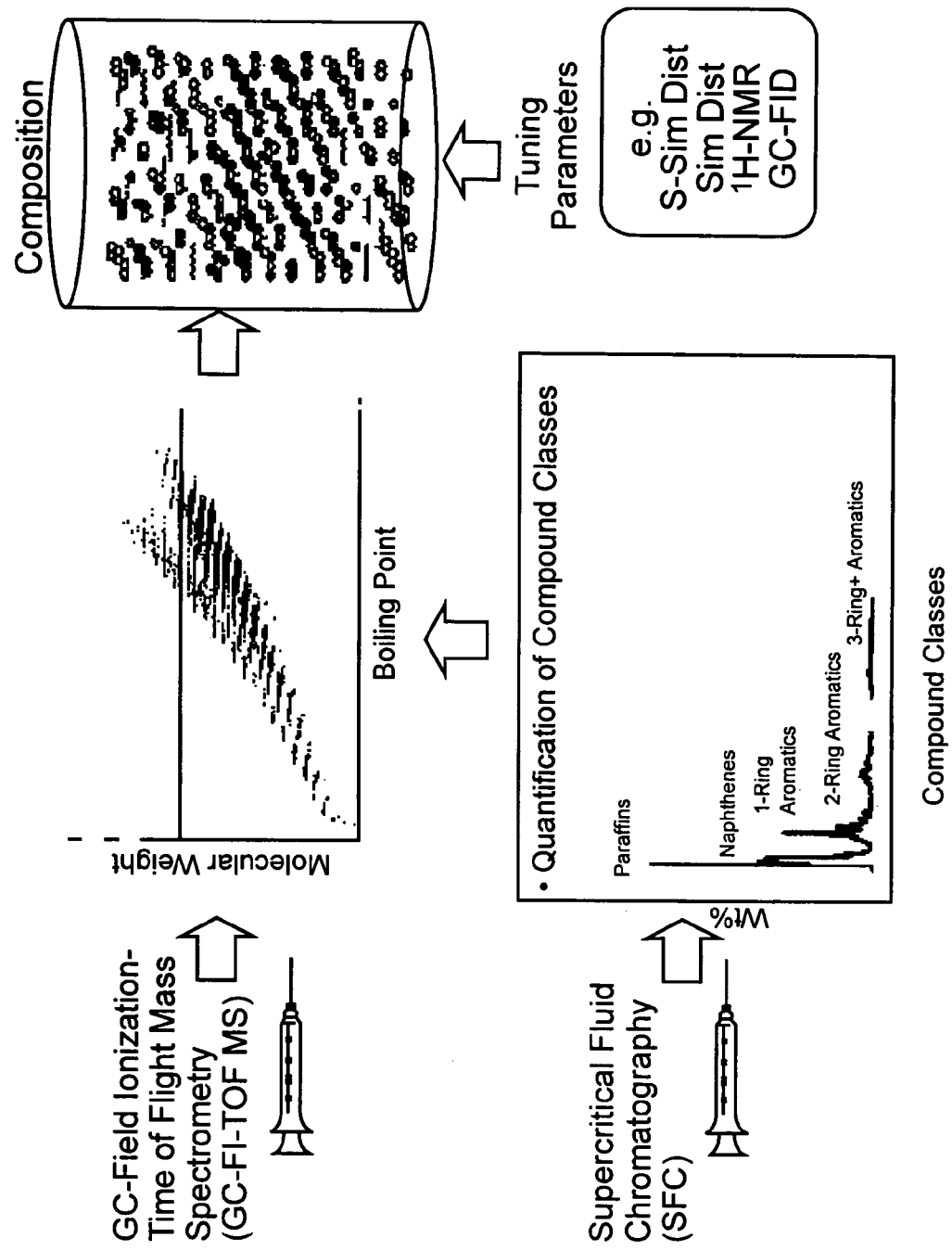
FIG. 1 shows the overall protocol of Micro-Hydrocarbon Analysis.

Micro-Hydrocarbon Analysis (MHA) consists of two components as illustrated in FIG. 1. (I) Measurements (resolution, identification and quantification) of hydrocarbon composition by combining chromatographic separation, soft ionization (or non-fragmenting ionization), and high resolution and accurate mass analysis. In a preferred embodiment, chromatographic separation is performed by gas chromatography (GC), soft ionization is by field ionization (FI), high resolution and accurate mass analysis is performed by time-of-flight mass spectrometer. (II) Reconciliation of other analytical measurements to generate model of composition. In preferred embodiments, other analytical measurements include supercritical fluid chromatography and/or liquid chromatography for paraffin, naphthene and aromatic ring type measurements, sulfur and nitrogen elemental analysis, simulated distillation and sulfur simulated distillation for yields, proton NMR for olefin content and gas chromatography for normal paraffin measurements.

I. Measurement of Composition by GC-FI-TOF Mass Spectrometer

Figure 2:
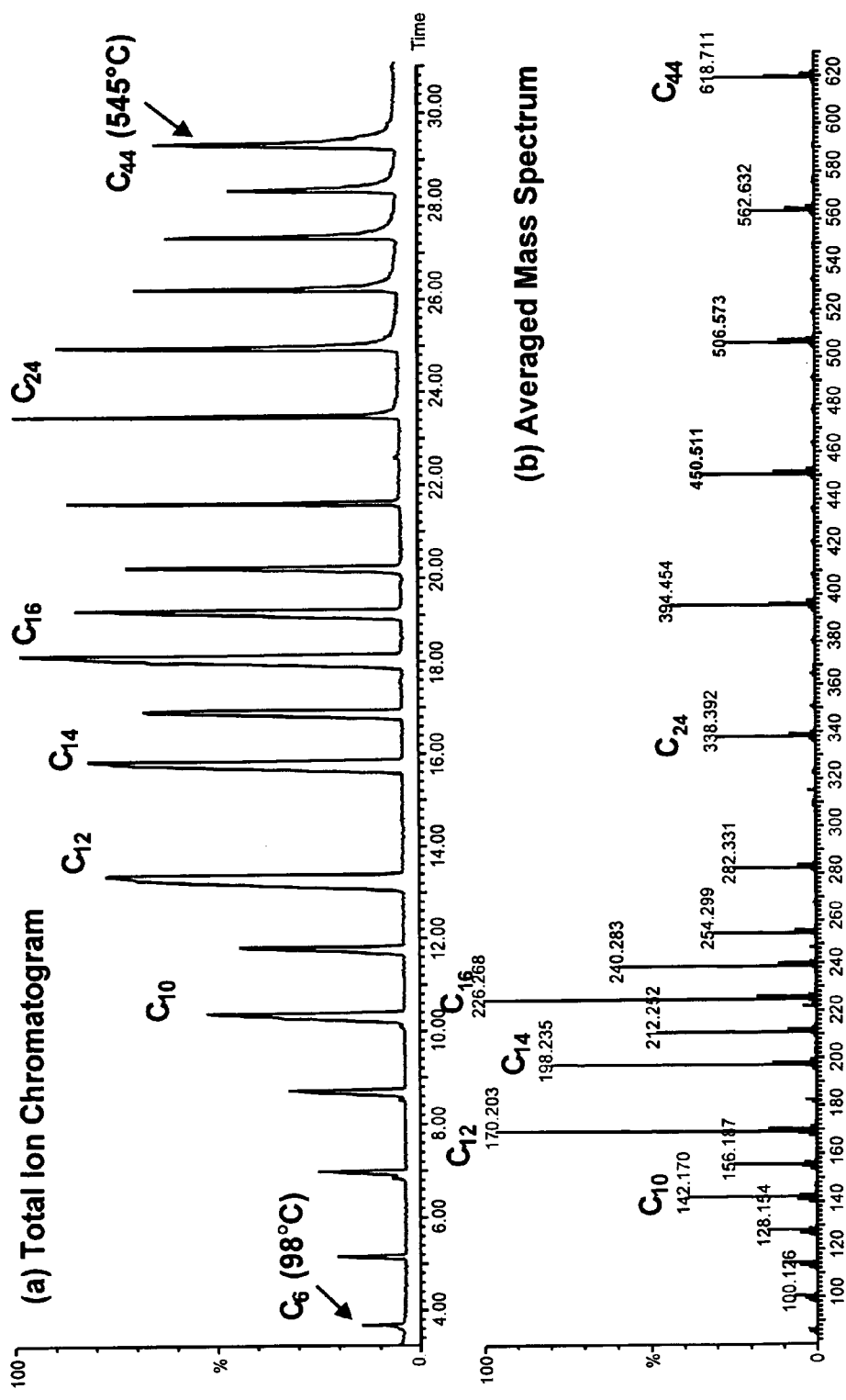
FIG. 2 shows an analysis of an n-paraffin mixture by a GC-FI-TOF-MS to give molecules over a wide boiling range.
Figure 3:
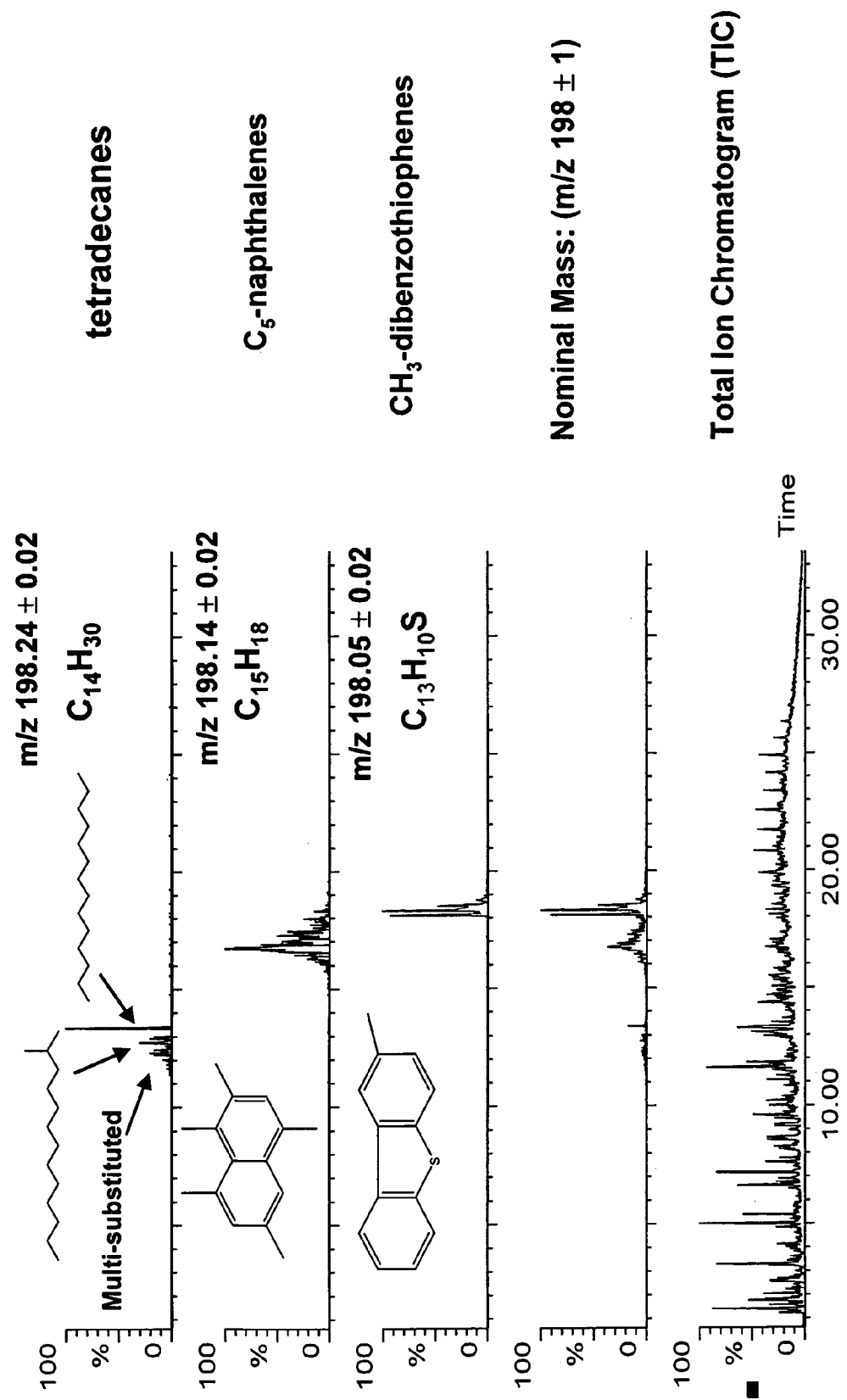
FIG. 3 shows that GC-FI-TOF-MS resolves isomer and isobaric molecules.
Figure 4:
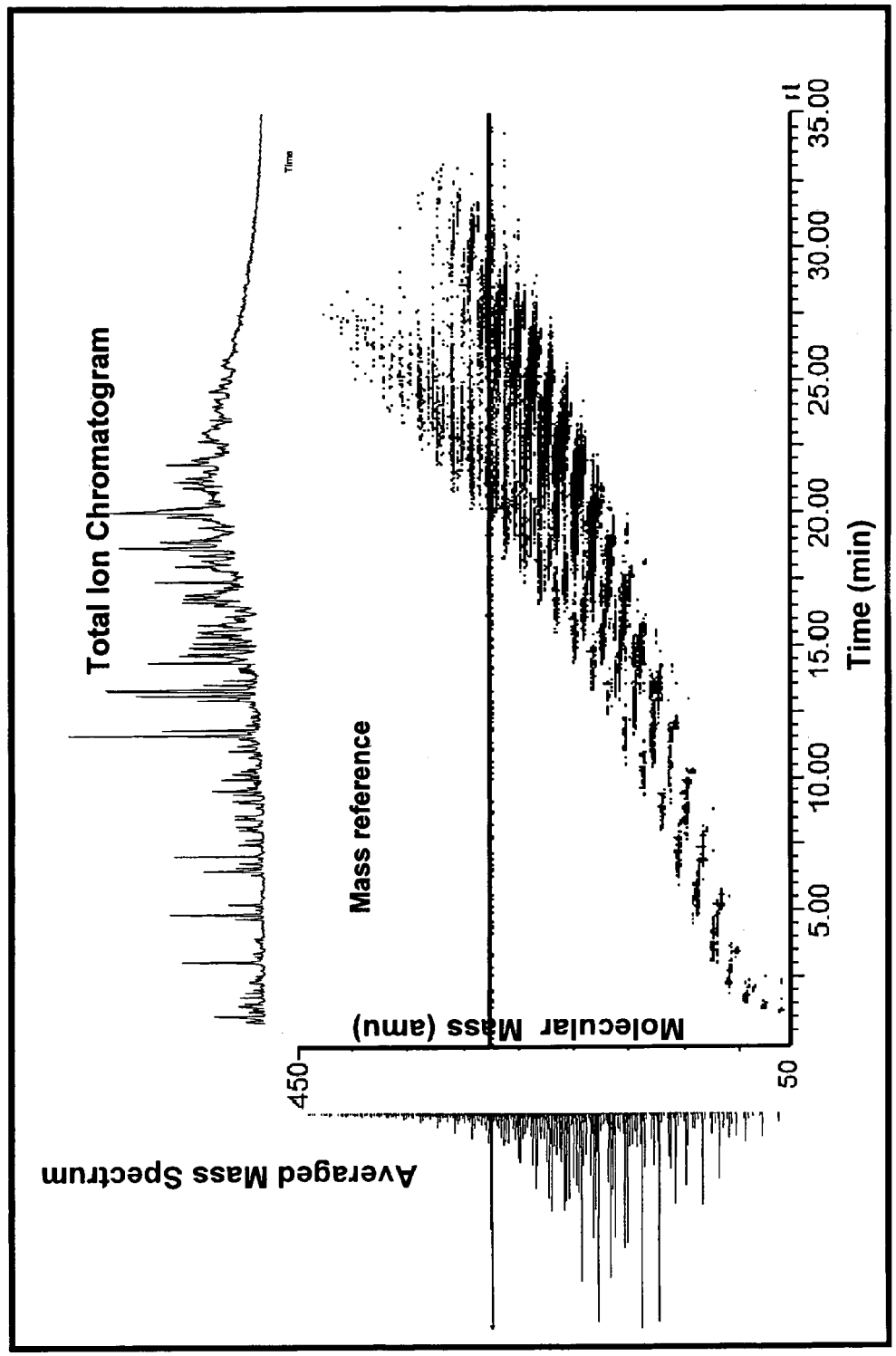
FIG. 4 shows that GC-FI-TOF-MS resolves about 1500 molecules in total liquid product.
Figure 5:
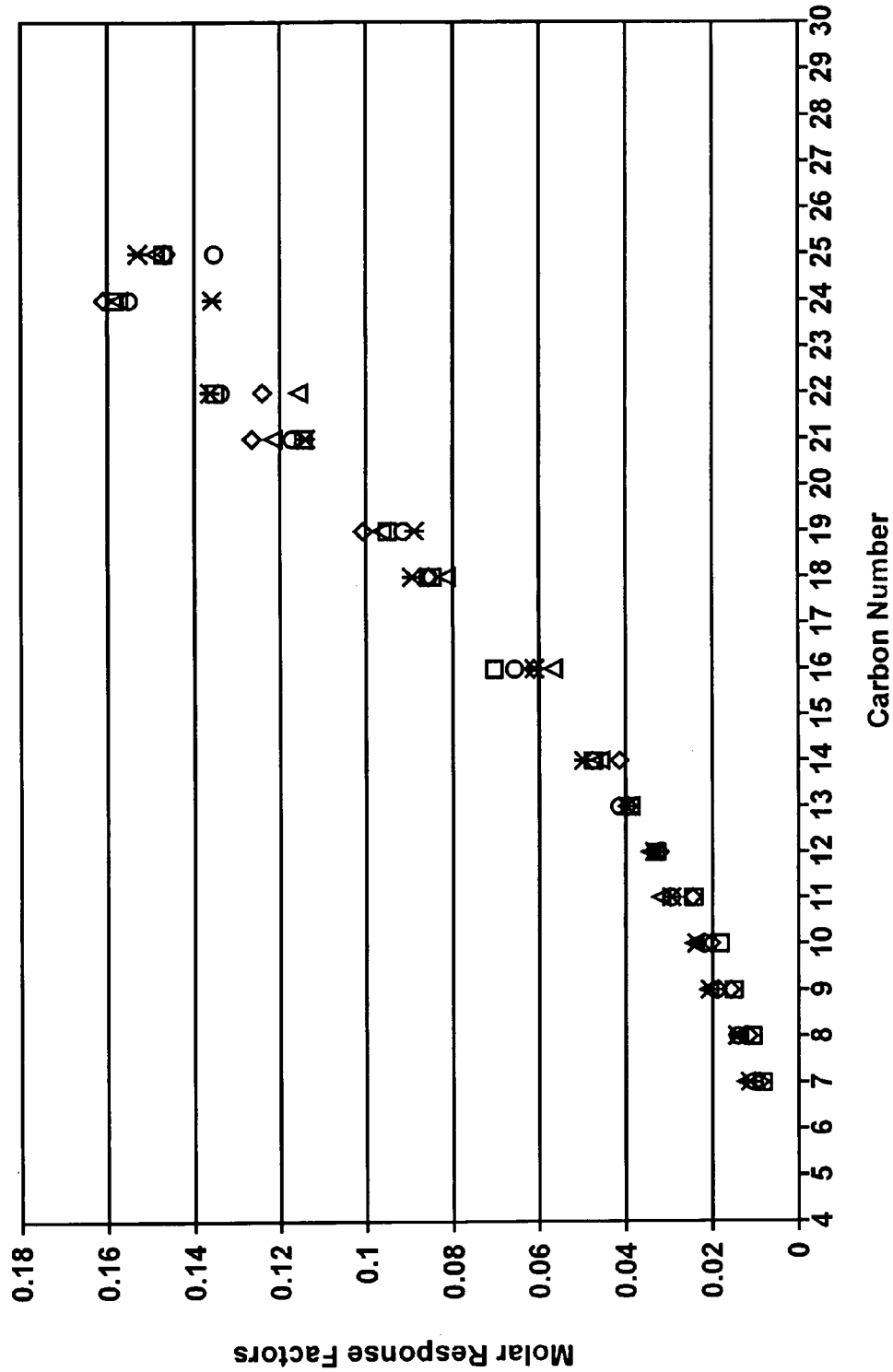
FIG. 5 shows the relative response factors of alkyl benzenes as a function of carbon numbers.

GC-FI-TOF mass spectrometer is the core component of Micro-Hydrocarbon Analysis. In this technique, GC is used to separate hydrocarbon species by boiling point or polarity depending on type of column used. The technique applies to a wide boiling point range as demonstrated in FIG. 2. Field ionization provides soft ionization of hydrocarbon molecules. Species co-elute in GC were resolved by TOF mass spectrometer. TOF-MS resolves isobaric molecules (molecules share the same nominal mass but different in exact masses, e.g. $C/H_{12}$ and $C_2H_8/S$ doublets with $\Delta M=93.9$ mDa and 90.5 mDa, respectively) by high mass resolving power ($M/\Delta M>5000$). Combined with GC separation, hard-to-resolve pairs, such as $C_3/SH_4$ ($\Delta M=3.4$ mDa), $N/^{13}CH$ ($\Delta M=8.2$ mDa) and $O/CH_4$ ($\Delta M=36.4$), can be completely or partially resolved as illustrated in FIG. 3. Resolution of isoparaffins versus normal paraffins and olefin versus cycloparaffins were based on chromatographic retention times. TOF MS also accurately determines the masses of the hydrocarbon components (with an error of less than 3 mDa). Elemental compositions of the masses can thus be determined. Table 1 demonstrates accurate mass analysis of paraffins and cyclic paraffins.

TABLE 1

The average errors in mass measurements are less than 3 mDa.

|  | Exp. Mass (Da) | Rel. Abun. | Calc. Mass (Da) | Error (mDa) | Rel. Error (ppm) | Formula |
| --- | --- | --- | --- | --- | --- | --- |
| Paraffins | 142.169 | 1.03 | 142.1722 | −3.2 | −22.2 | $C_{10}H_{22}$ |
|  | 156.1867 | 2.18 | 156.1878 | −1.1 | −7 | $C_{11}H_{24}$ |
|  | 170.202 | 3.69 | 170.2035 | −1.5 | −8.5 | $C_{12}H_{26}$ |
|  | 184.2189 | 6.71 | 184.2191 | −0.2 | −1.1 | $C_{13}H_{28}$ |
|  | 198.2345 | 11.3 | 198.2348 | −0.3 | −1.3 | $C_{14}H_{30}$ |
|  | 212.2507 | 15.25 | 212.2504 | 0.3 | 1.4 | $C_{15}H_{32}$ |
|  | 226.2659 | 16.14 | 226.2661 | −0.2 | −0.7 | $C_{16}H_{34}$ |
|  | 240.2827 | 13.15 | 240.2817 | 1 | 4.2 | $C_{17}H_{36}$ |
|  | 254.2956 | 11.1 | 254.2974 | −1.8 | −6.9 | $C_{18}H_{38}$ |
|  | 268.313 | 9.02 | 268.313 | 0 | 0 | $C_{19}H_{40}$ |
|  | 282.3279 | 7.84 | 282.3287 | −0.8 | −2.7 | $C_{20}H_{42}$ |
|  | 296.3392 | 4.74 | 296.3443 | −5.1 | −17.2 | $C_{21}H_{44}$ |
|  | 310.3622 | 2.35 | 310.36 | 2.2 | 7.2 | $C_{22}H_{46}$ |
|  | 324.3755 | 1.31 | 324.3756 | −0.1 | −0.3 | $C_{23}H_{48}$ |
| Cycloparaffins | 126.1498 | 2.05 | 126.1409 | 8.9 | 70.9 | $C_9H_{18}$ |
|  | 140.1623 | 4.44 | 140.1565 | 5.8 | 41.4 | $C_{10}H_{20}$ |
|  | 154.1748 | 7.04 | 154.1722 | 2.6 | 17.2 | $C_{11}H_{22}$ |
|  | 168.189 | 12.05 | 168.1878 | 1.2 | 7.1 | $C_{12}H_{24}$ |
|  | 182.2032 | 25.37 | 182.2035 | −0.3 | −1.4 | $C_{13}H_{26}$ |
|  | 196.219 | 43.36 | 196.2191 | −0.1 | −0.5 | $C_{14}H_{28}$ |
|  | 210.2352 | 70.65 | 210.2348 | 0.4 | 2.1 | $C_{15}H_{30}$ |
|  | 224.2508 | 100 | 224.2504 | 0.4 | 1.8 | $C_{16}H_{32}$ |
|  | 238.2669 | 91.71 | 238.2661 | 0.8 | 3.6 | $C_{17}H_{34}$ |
|  | 252.2824 | 85.22 | 252.2817 | 0.7 | 2.8 | $C_{18}H_{36}$ |
|  | 266.2968 | 75.44 | 266.2974 | −0.6 | −2.1 | $C_{19}H_{38}$ |
|  | 280.3127 | 61.34 | 280.313 | −0.3 | −1.1 | $C_{20}H_{40}$ |
|  | 294.3276 | 39.07 | 294.3287 | −1.1 | −3.6 | $C_{21}H_{42}$ |
|  | 308.3423 | 25.74 | 308.3443 | −2 | −6.5 | $C_{22}H_{44}$ |
|  | 322.3575 | 15.12 | 322.36 | −2.5 | −7.6 | $C_{23}H_{46}$ |
|  | 336.3747 | 8.95 | 336.3756 | −0.9 | −2.7 | $C_{24}H_{48}$ |
|  | 350.39 | 6.17 | 350.3913 | −1.3 | −3.6 | $C_{25}H_{50}$ |
|  | 364.3989 | 3.32 | 364.4069 | −8 | −22 | $C_{26}H_{52}$ |
|  | 378.4206 | 2.57 | 378.4226 | −2 | −5.2 | $C_{27}H_{54}$ |
|  | 392.4295 | 1.61 | 392.4382 | −8.7 | −22.2 | $C_{28}H_{56}$ |

Quantification of GC-FI-TOF data is carried out in two ways. First response factors of carbon numbers (or molecular weight) were determined using a mixture of alkyl benzene standard ($C_7$ to $C_{25}$). Second the total Hydrocarbon classes, paraffins, naphthenes, 1-ring aromatics, 2-ring aromatics and 3-ring+aromatics were normalized to that determined by high-resolution supercritical fluid chromatography or other chromatographic techniques.

Reduction of GC-FI-TOF data is based on defined retention time window and accurate mass window for various hydrocarbon species. The measurement generates a composition that will be further reconciliated with other analytical measurements.

Long term repeatability of MHA was studied on both alkyl benzene standard and on total liquid products from Catalytic Cracking experiments. Field Ionization is the major source of uncertainty in GC-FI-TOF measurement. FI sensitivity varies with molecular weight and molecular types. It also depends on the type of emitters used in the experiments. For practical applications, a mixture of alkyl benzenes ($C_7$ to $C_{25}$) are analyzed before and after a series of sample runs. In addition to calibrate carbon number response factors, the analysis also corrects fluctuations in GC retention time and MS measurement.

TABLE 2

Mole response factors (RF) of $C_7$ to $C_{25}$ alkyl benzene over a two-month period. The average Relative Standard Deviation (RSD) within an experimental set are largely less than 6%. The RF variation across the two-month period ranges from 5 to 15% RSD. The results demonstrate the necessity of alkyl benzene calibration for each set of experiment.

| C# | 7 | 8 | 9 | 10 | 11 | 12 | 13 | 14 | 15 | 16 | 17 | 18 |
|---|---|---|---|---|---|---|---|---|---|---|---|---|
| G030268 | 0.12 | 0.17 | 0.233 | 0.294 | 0.36 | 0.439 | 0.517 | 0.611 | 0.772 | 0.932 | 1.099 | 1.265 |
| G030273 | 0.158 | 0.212 | 0.283 | 0.329 | 0.407 | 0.465 | 0.52 | 0.669 | 0.801 | 0.932 | 1.135 | 1.338 |
| G030278 | 0.16 | 0.214 | 0.295 | 0.346 | 0.398 | 0.473 | 0.583 | 0.723 | 0.812 | 0.902 | 1.104 | 1.306 |
| G030283 | 0.154 | 0.194 | 0.264 | 0.314 | 0.386 | 0.463 | 0.529 | 0.683 | 0.795 | 0.906 | 1.112 | 1.317 |
| G030288 | 0.142 | 0.208 | 0.275 | 0.318 | 0.385 | 0.456 | 0.56 | 0.694 | 0.79 | 0.886 | 1.105 | 1.324 |
| G030292 | 0.142 | 0.193 | 0.244 | 0.309 | 0.375 | 0.433 | 0.518 | 0.641 | 0.74 | 0.839 | 1.065 | 1.29 |
| AVG | 0.146 | 0.199 | 0.266 | 0.318 | 0.385 | 0.455 | 0.538 | 0.67 | 0.785 | 0.9 | 1.103 | 1.307 |
| RSD | 10.2 | 8.3 | 8.9 | 5.6 | 4.3 | 3.4 | 5.1 | 5.9 | 3.3 | 3.8 | 2.1 | 2.0 |
| G030335 | 0.162 | 0.211 | 0.289 | 0.373 | 0.474 | 0.55 | 0.669 | 0.739 | 0.851 | 0.962 | 1.15 | 1.338 |
| G030339 | 0.147 | 0.21 | 0.282 | 0.36 | 0.436 | 0.506 | 0.581 | 0.691 | 0.842 | 0.992 | 1.12 | 1.247 |
| AVG | 0.154 | 0.21 | 0.285 | 0.366 | 0.455 | 0.528 | 0.625 | 0.715 | 0.846 | 0.977 | 1.135 | 1.293 |
| % RSD | 6.8 | 0.4 | 1.6 | 2.7 | 5.8 | 5.9 | 10.0 | 4.7 | 0.7 | 2.2 | 1.9 | 5.0 |
| G030341 | 0.158 | 0.212 | 0.239 | 0.35 | 0.436 | 0.476 | 0.518 | 0.565 | 0.763 | 0.962 | 1.198 | 1.435 |
| G030344 | 0.152 | 0.209 | 0.292 | 0.338 | 0.407 | 0.458 | 0.56 | 0.7 | 0.825 | 0.95 | 1.148 | 1.347 |
| G030345 | 0.149 | 0.203 | 0.252 | 0.363 | 0.425 | 0.507 | 0.587 | 0.736 | 0.844 | 0.953 | 1.152 | 1.352 |
| AVG | 0.153 | 0.208 | 0.261 | 0.35 | 0.423 | 0.48 | 0.555 | 0.667 | 0.811 | 0.955 | 1.166 | 1.378 |
| % RSD | 2.8 | 2.2 | 10.6 | 3.6 | 3.4 | 5.2 | 6.2 | 13.5 | 5.2 | 0.6 | 2.4 | 3.6 |
| G030410 | 0.129 | 0.187 | 0.267 | 0.327 | 0.415 | 0.499 | 0.595 | 0.668 | 0.831 | 0.995 | 1.114 | 1.234 |
| G030415 | 0.151 | 0.208 | 0.277 | 0.349 | 0.428 | 0.507 | 0.589 | 0.698 | 0.834 | 0.971 | 1.12 | 1.269 |
| G030421 | 0.134 | 0.195 | 0.265 | 0.329 | 0.404 | 0.507 | 0.599 | 0.702 | 0.849 | 0.997 | 1.145 | 1.294 |
| AVG | 0.138 | 0.197 | 0.27 | 0.335 | 0.416 | 0.504 | 0.594 | 0.689 | 0.838 | 0.987 | 1.127 | 1.266 |
| % RSD | 8.3 | 5.5 | 2.5 | 3.6 | 2.9 | 0.8 | 0.8 | 2.7 | 1.2 | 1.4 | 1.5 | 2.4 |
| G030422 | 0.102 | 0.149 | 0.168 | 0.267 | 0.352 | 0.421 | 0.558 | 0.795 | 0.926 | 1.057 | 1.33 | 1.604 |
| G030423 | 0.111 | 0.158 | 0.207 | 0.282 | 0.361 | 0.421 | 0.557 | 0.647 | 0.787 | 0.928 | 1.157 | 1.385 |
| G030425 | 0.119 | 0.176 | 0.239 | 0.307 | 0.382 | 0.454 | 0.585 | 0.682 | 0.819 | 0.955 | 1.129 | 1.302 |
| AVG | 0.138 | 0.197 | 0.27 | 0.335 | 0.416 | 0.504 | 0.594 | 0.689 | 0.838 | 0.987 | 1.127 | 1.266 |
| % RSD | 6.2 | 6.8 | 13.1 | 6.0 | 3.7 | 3.9 | 2.7 | 11.3 | 8.7 | 6.9 | 9.7 | 12.3 |
| G030427 | 0.1 | 0.142 | 0.208 | 0.269 | 0.361 | 0.421 | 0.508 | 0.648 | 0.821 | 0.993 | 1.192 | 1.392 |
| G030430 | 0.101 | 0.149 | 0.206 | 0.263 | 0.334 | 0.402 | 0.49 | 0.615 | 0.778 | 0.942 | 1.081 | 1.22 |
| AVG | 0.101 | 0.145 | 0.207 | 0.266 | 0.347 | 0.411 | 0.499 | 0.631 | 0.799 | 0.967 | 1.137 | 1.306 |
| % RSD | 1.2 | 3.4 | 0.6 | 1.7 | 5.5 | 3.2 | 2.4 | 3.7 | 3.8 | 3.8 | 7.0 | 9.3 |
| G030507 | 0.117 | 0.164 | 0.229 | 0.287 | 0.381 | 0.439 | 0.555 | 0.644 | 0.775 | 0.905 | 1.116 | 1.326 |
| G030512 | 0.119 | 0.159 | 0.219 | 0.299 | 0.368 | 0.433 | 0.533 | 0.617 | 0.73 | 0.844 | 1.053 | 1.263 |
| AVG | 0.118 | 0.161 | 0.224 | 0.293 | 0.375 | 0.436 | 0.544 | 0.631 | 0.753 | 0.875 | 1.085 | 1.295 |
| % RSD | 0.9 | 2.1 | 3.1 | 2.8 | 2.6 | 1.0 | 2.9 | 3.1 | 4.2 | 5.0 | 4.1 | 3.5 |

| C# | 19 | 20 | 21 | 22 | 23 | 24 | 25 | Date | Time |
|---|---|---|---|---|---|---|---|---|---|
| G030268 | 1.476 | 1.697 | 1.917 | 1.999 | 2.227 | 2.456 | 2.802 | 28-Feb-2003 | 20:52:03 |
| G030273 | 1.474 | 1.671 | 1.868 | 1.999 | 2.102 | 2.205 | 2.715 | 01-Mar-2003 | 01:17:59 |
| G030278 | 1.413 | 1.608 | 1.804 | 1.874 | 2.127 | 2.38 | 2.655 | 01-Mar-2003 | 05:41:44 |
| G030283 | 1.419 | 1.609 | 1.799 | 2.04 | 2.249 | 2.457 | 2.68 | 01-Mar-2003 | 10:05:09 |
| G030288 | 1.489 | 1.662 | 1.836 | 2.156 | 2.238 | 2.32 | 2.617 | 01-Mar-2003 | 14:28:16 |
| G030292 | 1.486 | 1.637 | 1.788 | 2.244 | 2.366 | 2.489 | 2.715 | 01-Mar-2003 | 17:58:50 |
| AVG | 1.46 | 1.647 | 1.835 | 2.052 | 2.218 | 2.385 | 2.697 | | |
| RSD | 2.4 | 2.2 | 2.7 | 6.4 | 4.3 | 4.5 | 2.4 | | |
| G030335 | 1.568 | 1.683 | 1.797 | 1.79 | 1.983 | 2.175 | 2.382 | 24-Mar-2003 | 13:41:46 |
| G030339 | 1.477 | 1.628 | 1.779 | 1.909 | 2.093 | 2.276 | 2.65 | 24-Mar-2003 | 10:04:37 |
| AVG | 1.523 | 1.655 | 1.788 | 1.85 | 2.038 | 2.226 | 2.516 | | |
| % RSD | 4.2 | 2.3 | 0.7 | 4.5 | 3.8 | 3.2 | 7.5 | | |
| G030341 | 1.692 | 1.853 | 2.014 | 2.038 | 2.167 | 2.297 | 2.206 | 27-Mar-2003 | 11:53:45 |
| G030344 | 1.485 | 1.662 | 1.838 | 1.893 | 2.119 | 2.345 | 2.561 | 27-Mar-2003 | 14:52:55 |
| G030345 | 1.535 | 1.644 | 1.753 | 2.144 | 2.269 | 2.395 | 2.299 | 27-Mar-2003 | 15:47:48 |

TABLE 2-continued

| | | | | | | | | | |
|---|---|---|---|---|---|---|---|---|---|
| AVG | 1.571 | 1.719 | 1.868 | 2.025 | 2.185 | 2.346 | 2.355 | | |
| % RSD | 6.9 | 6.7 | 7.1 | 6.2 | 3.5 | 2.1 | 7.8 | | |
| G030410 | 1.468 | 1.671 | 1.874 | 2.044 | 2.204 | 2.365 | 2.539 | 04-Apr-2003 | 17:07:09 |
| G030415 | 1.386 | 1.649 | 1.911 | 2.011 | 2.179 | 2.346 | 2.49 | 04-Apr-2003 | 21:38:16 |
| G030421 | 1.511 | 1.688 | 1.865 | 2.073 | 2.153 | 2.233 | 2.509 | 05-Apr-2003 | 03:01:40 |
| AVG | 1.455 | 1.669 | 1.883 | 2.043 | 2.179 | 2.315 | 2.512 | | |
| % RSD | 4.4 | 1.2 | 1.3 | 1.5 | 1.2 | 3.1 | 1.0 | | |
| G030422 | 1.694 | 1.765 | 1.837 | 1.865 | 2.053 | 2.241 | 2.41 | 10-Apr-2003 | 15:26:12 |
| G030423 | 1.602 | 1.735 | 1.869 | 2.207 | 2.386 | 2.566 | 2.391 | 10-Apr-2003 | 16:08:29 |
| G030425 | 1.464 | 1.649 | 1.833 | 2.147 | 2.311 | 2.474 | 2.543 | 10-Apr-2003 | 17:55:50 |
| AVG | 1.455 | 1.669 | 1.883 | 2.043 | 2.179 | 2.315 | 2.512 | | |
| % RSD | 7.9 | 3.6 | 1.0 | 8.9 | 8.0 | 7.3 | 3.3 | | |
| G030427 | 1.571 | 1.913 | 2.255 | 2.01 | 2.106 | 2.201 | 2.506 | 11-Apr-2003 | 13:01:04 |
| G030430 | 1.399 | 1.7 | 2 | 1.96 | 2.197 | 2.435 | 3.061 | 11-Apr-2003 | 15:42:46 |
| AVG | 1.485 | 1.806 | 2.127 | 1.985 | 2.151 | 2.318 | 2.784 | | |
| % RSD | 8.2 | 8.3 | 8.5 | 1.8 | 3.0 | 7.1 | 14.1 | | |
| G030507 | 1.516 | 1.679 | 1.841 | 2.121 | 2.304 | 2.486 | 2.639 | 01-May-2003 | 15:56:15 |
| G030512 | 1.487 | 1.697 | 1.907 | 2.174 | 2.326 | 2.479 | 2.78 | 01-May-2003 | 20:31:12 |
| AVG | 1.502 | 1.688 | 1.874 | 2.147 | 2.315 | 2.482 | 2.709 | | |
| % RSD | 1.4 | 0.8 | 2.5 | 1.7 | 0.7 | 0.2 | 3.7 | | |

TABLE 3

Long term reproducibility on analyses of a liquid hydrocarbon product. Variations in naphtha and middle distillate yields are approximately 1.2 and 0.7%, respectively. Variations in Octane and Cetane Number are approximately 0.7 and 1 unit, respectively.

| | Date | | | | | | | | | |
|---|---|---|---|---|---|---|---|---|---|---|
| | 01-Oct-2002 | 27-Feb-2003 | 04-Mar-2003 | 12-Mar-2003 | 24-Mar-2003 | 27-Mar-2003 | Apr. 7, 2003 | Apr. 16, 2003 | Aver- | |
| | Filename | | | | | | | | | |
| | G021004 | G030260 | G030304 | G030319 | G030336 | G030342 | G030420 | G030429 | age | STD |
| Gravity | 40.7 | 40.5 | 40.1 | 40.1 | 40.4 | 39.9 | 39.6 | 39.3 | 40.1 | 0.5 |
| Sulfur | 0.42 | 0.49 | 0.44 | 0.43 | 0.52 | 0.53 | 0.47 | 0.47 | 0.5 | 0.0 |
| aliphatic S | 0.04 | 0.14 | 0.05 | 0.05 | 0.05 | 0.05 | 0.05 | 0.07 | 0.1 | 0.0 |
| saturates | 24.2 | 24.4 | 25.2 | 24.3 | 24.3 | 24.3 | 25.4 | 25.2 | 24.6 | 0.5 |
| paraffins (norfiso) | 3.0 | 2.0 | 2.3 | 2.6 | 2.5 | 2.8 | 2.9 | 2.8 | 2.6 | 0.3 |
| | 16.7 | 17.6 | 17.4 | 17.1 | 17.2 | 16.9 | 16.8 | 16.8 | 17.1 | 0.3 |
| 1-ring naph | 4.2 | 4.5 | 4.6 | 4.3 | 4.3 | 4.4 | 4.5 | 4.5 | 4.4 | 0.1 |
| 2-ring naph | 0.1 | 0.1 | 0.7 | 0.1 | 0.1 | 0.1 | 0.8 | 0.7 | 0.3 | 0.3 |
| 3-ring naph | 0.3 | 0.2 | 0.2 | 0.2 | 0.2 | 0.2 | 0.3 | 0.2 | 0.2 | 0.0 |
| arom + sul | 50.0 | 50.0 | 49.9 | 49.9 | 50.0 | 50.0 | 50.0 | 50.0 | 50.0 | 0.0 |
| 1-Ring Arom | 50.8 | 50.4 | 49.8 | 50.6 | 50.7 | 50.6 | 49.6 | 49.7 | 50.3 | 0.5 |
| 2-Ring Arom | 12.0 | 12.5 | 12.1 | 12.2 | 12.2 | 12.3 | 12.0 | 12.2 | 12.2 | 0.2 |
| 3-Ring Arom | 9.8 | 7.9 | 9.6 | 8.9 | 9.3 | 9.4 | 8.9 | 9.4 | 9.1 | 0.6 |
| 4-Ring Arom | 3.2 | 4.6 | 3.2 | 3.8 | 3.5 | 3.3 | 4.1 | 3.5 | 3.6 | 0.5 |
| H | 11.6 | 11.6 | 11.7 | 11.6 | 11.6 | 11.6 | 11.7 | 11.6 | 11.6 | 0.0 |
| Br no. | 48.2 | 45.7 | 44.7 | 46.1 | 46.6 | 46.0 | 44.4 | 43.9 | 45.7 | 1.4 |
| RON (65–430 F.) | 91.3 | 91.4 | 91.0 | 91.3 | 91.5 | 91.7 | 91.1 | 91.2 | 91.3 | 0.2 |
| MON (65–430 F.) | 81.5 | 82.9 | 80.8 | 81.1 | 81.3 | 81.3 | 80.9 | 80.8 | 81.3 | 0.7 |
| ole | 25.8 | 25.6 | 24.9 | 25.7 | 25.8 | 25.7 | 24.7 | 24.8 | 25.4 | 0.5 |
| % CA | 44.9 | 44.7 | 44.1 | 44.5 | 44.6 | 44.4 | 43.8 | 44.1 | 44.4 | 0.4 |
| Pour pt (° C.) | 12.9 | 13.1 | 11.5 | 12.8 | 11.2 | 11.4 | 16.4 | 13.8 | 12.9 | 1.7 |
| Cloud pt (° C.) | 55.9 | 60.2 | 57.8 | 59.1 | 58.1 | 56.4 | 59.9 | 57.0 | 58.0 | 1.6 |
| Freeze pt (° C.) | 55.9 | 60.2 | 57.8 | 59.1 | 58.1 | 56.4 | 59.9 | 57.0 | 58.0 | 1.6 |
| CI (430–650 F.) | 24.5 | 25.4 | 25.0 | 26.0 | 25.4 | 26.0 | 25.9 | 25.8 | 25.5 | 0.5 |
| CN (430–650 F.) | 16.0 | 17.3 | 16.9 | 18.4 | 17.5 | 18.5 | 18.3 | 18.1 | 17.6 | 0.9 |
| Naphtha (Wt %) | 57.3 | 60.9 | 59.1 | 58.4 | 59.0 | 58.2 | 58.0 | 59.0 | 58.8 | 1.1 |
| Middle Dist (Wt %) | 24.3 | 23.4 | 24.7 | 25.2 | 24.4 | 25.2 | 24.2 | 24.5 | 24.5 | 0.6 |

II. Reconciliation of GC-FI-TOF Mass Spectrometer Data

The final step of Micro-Hydrocarbon Analysis is to reconcile analytical measurements to the model-of-composition. In particular, the model-of-composition must reproduce all measurements in the analytical protocol as closely as possible, and at the same time satisfy a set of property balances, e.g. mass and is elemental composition. A number of targets were used for the data tuning (or data reconciliation). The total olefin content is tuned to that measured by proton NMR. Hydrocarbon and S yields were tuned to that measured experimentally by gas chromatography simulated distillation (SIMDIS and S-SIMDIS), calculated N and S contents were tuned to that measured by elemental analysis, etc.

One embodiment of this reconciliation procedure is to treat it as a constrained optimization problem: we optimize the model-of-composition's fidelity to the test results of the analytical protocol subject to the property balance constraints.

Another embodiment of the reconciliation procedure is successive substitution, an iterative procedure in which the model-of-composition is adjusted to match the results of the analytical protocol in a prescribed sequence until changes in the model-of-composition between iterations fall below a prescribed tolerance. The detailed description of model of composition and data reconciliation can be found in the attached appendix.

III. Generation of Cut Composition from MHA

One significant advantage of MHA is that it enables the generation of boiling point cut composition without physically distilling the sample. Tables 4 and 5 show the compositions of naphtha and middle distillate predicted by MHA virtual cut (cut based on calculated boiling point of the molecules) and that based on measurements of physically distilled cuts. The results agree well.

TABLE 4

Detailed Comparisons of the molecular compositions and calculated properties of the distilled naphtha cut (65-430° F.)

|  | GC-PIONA | MHA naphtha cut | MHA virtual naphtha cut |
| --- | --- | --- | --- |
| API | 53.5 | 53.32 | 52.61 |
| RON | N/A | 90.3 | 90.59 |
| MON | N/A | 81.76 | 81.84 |
| $H_2$ % | N/A | 12.83 | 12.76 |
| S wt % | 0.05 | 0.1 | 0.06 |
| Paraffins sum | 23.15 | 19.25 | 20.32 |
| n-paraffins | 3.77 | 1.14 | 0.63 |
| i-paraffins | 19.38 | 18.11 | 19.63 |
| Naphthenes sum | 10.05 | 11.09 | 10.57 |
| 1-ring naphthene | 10.05 | 11.09 | 10.57 |
| 2-ring naphthenes | 0 | 0.0 | 0.0 |
| Aromatics sum | 29.96 | 33.68 | 36.37 |
| Benzenes | N/A | 29.03 | 29.91 |
| Naphthalenes | N/A | 0.8 | 0.66 |
| Naphth-/Olef-benzenes | N/A | 3.85 | 5.66 |
| Indenes | N/A | 0.0 | 0.14 |
| Olefins sum | 30.59 | 35.62 | 32.49 |
| Olefins | N/A | 25.2 | 23.08 |
| Naphtheno-olefins | N/A | 3.99 | 3.59 |
| Di-olefins | N/A | 5.66 | 5.12 |
| Other olefins | N/A | 0.77 | 0.7 |
| Sum of C13+ | 6.23 | N/A | N/A |

TABLE 5

Detailed comparison of the molecular compositions and properties of mid-distillate (430-650° F. distilled cut)

|  | Experimental (430-650 cut) | MHA (430-650 cut) | MHA (virtual 430-650 cut) |
| --- | --- | --- | --- |
| API gravity | 18.6 | 18.49 | 17.02 |
| Estimated Cetane # | 18.4 | 12.04 | 15.08 |
| S wt % | 0.697 | 0.88 | 0.78 |
| $H_2$ wt % | 9.95 | 9.74 | 9.66 |
| Saturates wt % | 21.98 | 19.52 | 19.09 |
| Paraffins wt % | 10.42 | 10.21 | 14.08 |
| N-paraffins wt % | N/A | 2.53 | 5.28 |
| 1-ring naphthene | N/A | 7.82 | 3.9 |
| 2-ring naphthene | N/A | 0.84 | 0.62 |
| 3-ring naphthene | N/A | 0.66 | 0.49 |
| Aromatics wt % | 77.77 | 80.26 | 80.7 |
| 1-ring aromatic | N/A | 27.17 | 21.98 |
| 2-ring aromatic | N/A | 45.05 | 45.85 |
| 3-ring aromatic | N/A | 7.87 | 12.85 |
| 4-ring aromatic | N/A | 0.17 | 0.03 |
| Olefins wt % | N/A | 2.63 | 1.73 |
| Bromine # | N/A | 2.53 | 1.46 |
| Refractive index | N/A | 1.5239 | 1.5311 |

APPENDIX

The Model-of-Composition

1. Introduction

Petroleum streams are complex mixtures of hydrocarbons containing many thousands of distinct molecular species. These streams include any hydrocarbon stream from processes that change petroleum's molecular composition. The streams are so complex, and have so many distinct molecular species that any molecular description of the composition is essentially a model—a model-of-composition.

2. Organizing the Model-of-Composition

Figure 6:
FIG. 6 shows 145 homologous series cores found in petroleum.

The model-of-composition is organized initially into four major groups: saturates, aromatics, sulfides and polar molecules. Olefins are rare in crude petroleum, but are generated in refining processes that involve thermal or catalytic cracking and comprise a fifth major group. Within each major group, we organize molecules by homologous series. A homologous series is a molecular group that shares the same chemical structure (core), but has alkyl side chains of differing carbon number, arrangement and branching patterns. FIG. 6 shows 145 homologous series cores found in petroleum. FIG. 7 shows sample homologous series of benzene, naphthalene, fluorene, and dibenzothiophene.

It is convenient to organize hydrocarbon homologous series by hydrogen deficiency. Hydrogen deficiency can be organized into 14 classes (the primary x-classes) according to the formula:

$$x\text{-class}=(-14)+\text{mod}(MW,14). \qquad 1.$$

The x-class is the remainder of the "nominal" molecular weight divided by 14. By convention the values −12, −13, −14 are replaced with 2 1 0 so x-class runs from −11 to 2. Although several homologous series present in petroleum share the same x-class, all molecules within each homologous series share the same x-class because the molecular weight of a —$CH_2$— group is 14.

Saturate Molecules

Saturate molecules contain only aliphatic carbons and hydrogen and their x-classes take the even integers −12, −10, −8, −6, −4, −2, 0 2. FIG. 8 show sample saturates arranged by x-class. Reading from right to left the molecules are 0 ring saturates, 1 ring saturates, 2 ring saturates etc. Notice that there are many similar (but related) molecules present in each x-class. These molecules are structural isomers sharing the identical mass and often very difficult to identify analytically in the complex mixture. A representative structure in each x-class (sometimes more than one) then becomes the model-of-composition. The preferred structures are shown in bold.

Aromatic Molecules

Aromatic molecules have carbon atoms in aromatic rings. Aromatic molecules found in petroleum often contain sulfur and non-basic nitrogen (—NH—) groups. We have organized aromatic molecules by ring class, i.e. 1, 2, 3 and 4+.

1 Ring Aromatic Molecules

FIG. 9 shows 1 ring aromatic cores arranged by x-class. Preferred structures are in bold. Some of these cores actually contain two aromatic rings separated by naphthenic rings or alkyl chains (x-class −4, −2, 0 in FIG. 9) but are predominantly 1 ring in character. The alternate structures in x-class −4, −2, 0 have 4, 5 and 6 naphthenic rings, and are rare in petroleum. In the model-of-composition, thiophene is equivalent to an aromatic ring. Thiophenes (x-class −4, −2, 0)

are rare in crude petroleum, but are made in refining processes that involve thermal or catalytic cracking.

2 Ring Aromatic Molecules

Figure 10:
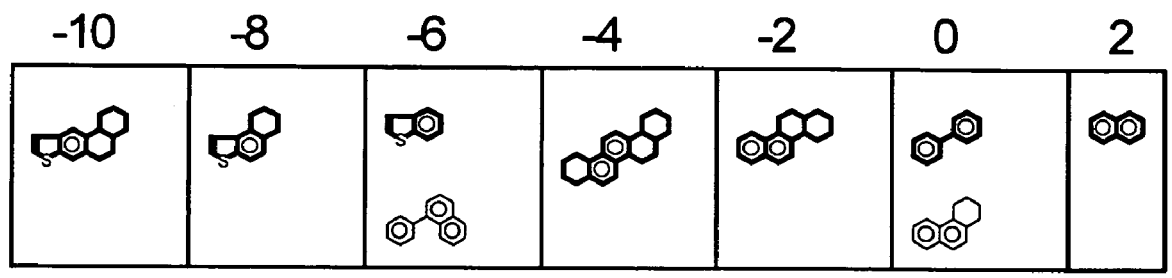
FIG. 10 shows 2 ring aromatic cores that have x-classes that take even integers −10, −8, −6, −4, −2, 0, 2.

Two ring aromatic cores shown in FIG. 10 have x-classes that take the even integers −10, −8, −6, −4, −2, 0, 2. Three of the preferred structures shown in bold are benzothiophenes (x-classes −10, −8, −6). In the model-of-composition, a thiophene group is equivalent to an aromatic ring. Molecules containing the benzothiophene core (x-class −6 in FIG. 10) are much more common in petroleum than those containing less preferred structure, phenylnaphthalene. Biphenyl cores (x-class −2) are more abundant in petroleum than are tetrahydrophenanthrene cores. However, in hydroprocessed petroleum streams tetrahydrophenanthrenes are more abundant than are biphenyls.

3 Ring Aromatic Molecules

Figure 11:
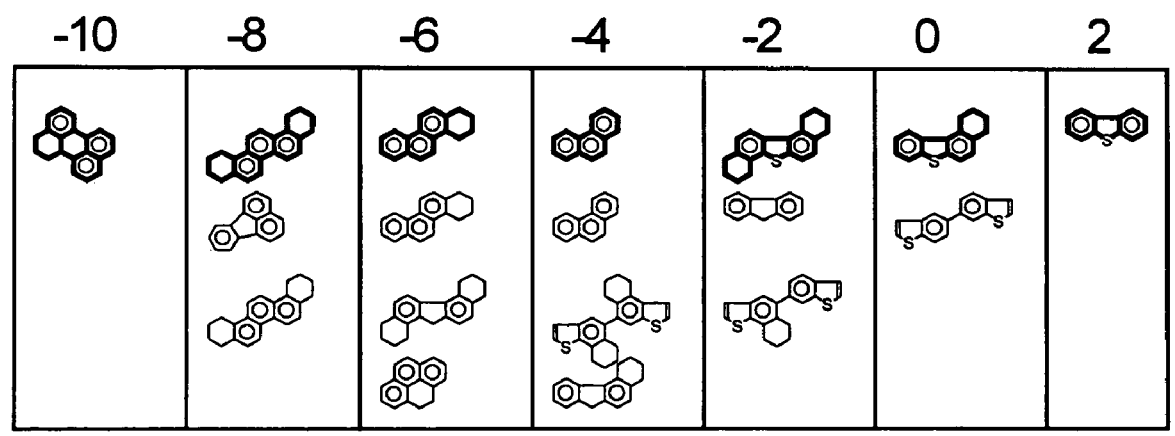
FIG. 11 shows 3 ring aromatic cores that have x-classes that take the even integers −10, −8, −6, −4, −2, 0, 2.

FIG. 11 have x-classes that take the even integers −10, −8, −6, −4, −2, 0, 2. Dibenzothiophenes (x-classes −2, 0, 2), abundant in petroleum, have three-ring aromatic character. Phenanthrene and anthracene (x-class −4) are both three-ring aromatics. Phenathrene is common in petroleum; anthracene is common in coal.

Figure 12:
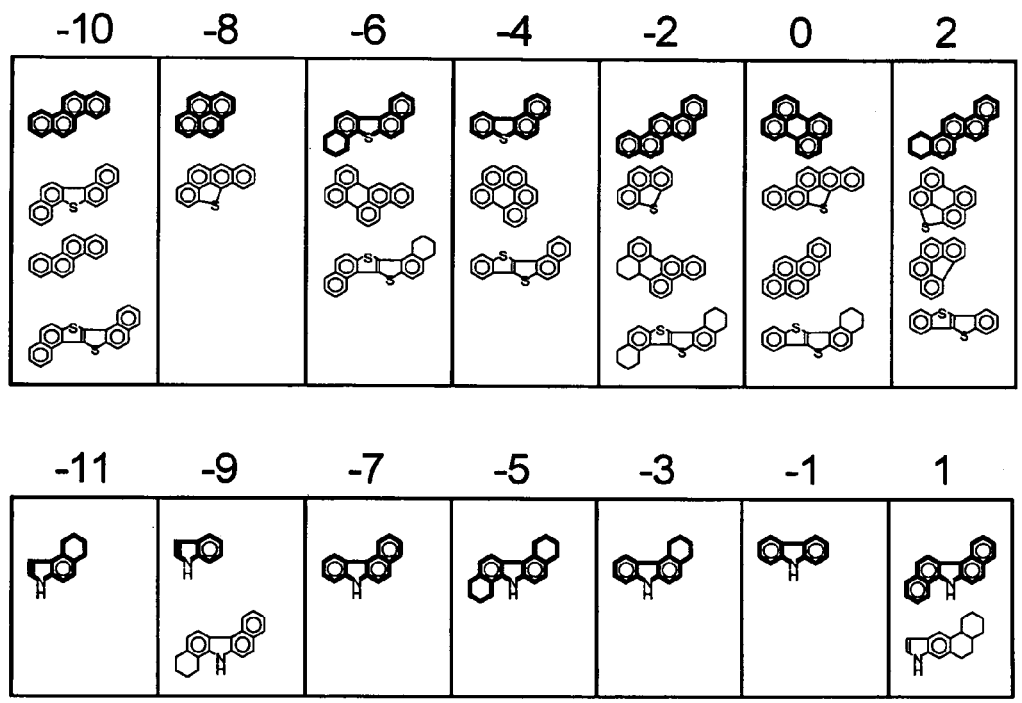
FIG. 12 shows 4 ring aromatic cores that have x-classes that take the even integers −10, −8, −6, −4, −2, 0, 2, and the odd integers −11, −9, −7, −5, −3, −1, 1.

4 Ring Aromatic Molecules 4 ring aromatic cores shown in FIG. 12 have x-classes that take the even integers −10, −8, −6, −4, −2, 0, 2, and the odd integers −11, −9, −7, −5, −3, −1, 1. Each of the odd x-class cores contains a non-basic nitrogen group (—NH—). In the model-of-composition, all aromatic molecules that have non-basic nitrogen take four ring aromatic characters. Several structures have one or two thiophenic sulfur groups. The homologous series containing benzopyrene cores (x-class 0) includes benzo(a)pyrene, a potent carcinogen.

Sulfide Molecules

Figure 13:
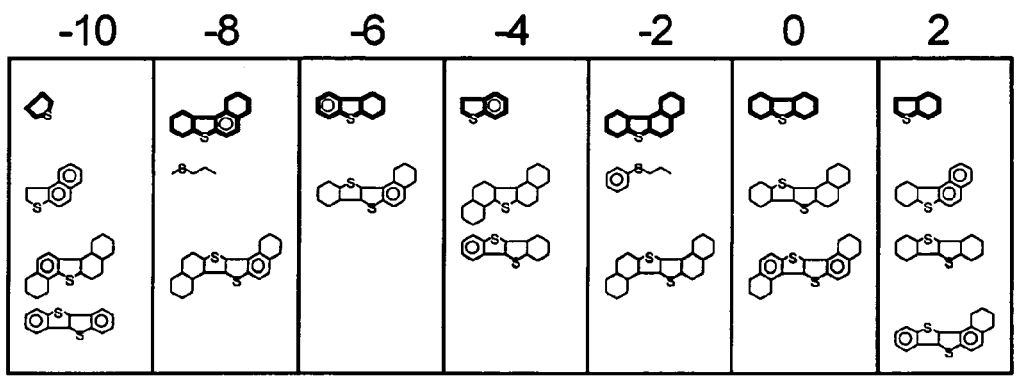
FIG. 13 shows the sulfide cores that have x-classes that take the even integers −10, −8, −6, −4, −2, 0, 2.

Sulfide molecules contain aliphatic sulfur, but they have neither oxygen nor nitrogen. The cores shown in FIG. 13 have x-classes that take the even integers −10, −8, −6, −4, −2, 0, 2. Preferred structures are in bold. Alkyl sulfides (x-class −8), and benzyl sulfides (x-class −2) are not preferred because they are rare in petroleum. Sulfide cores in the model-of-composition have either one or aliphatic sulfur groups. Some of these cores contain only aliphatic carbon; others contain both aliphatic and aromatic carbon.

Polar Molecules

Figure 14:
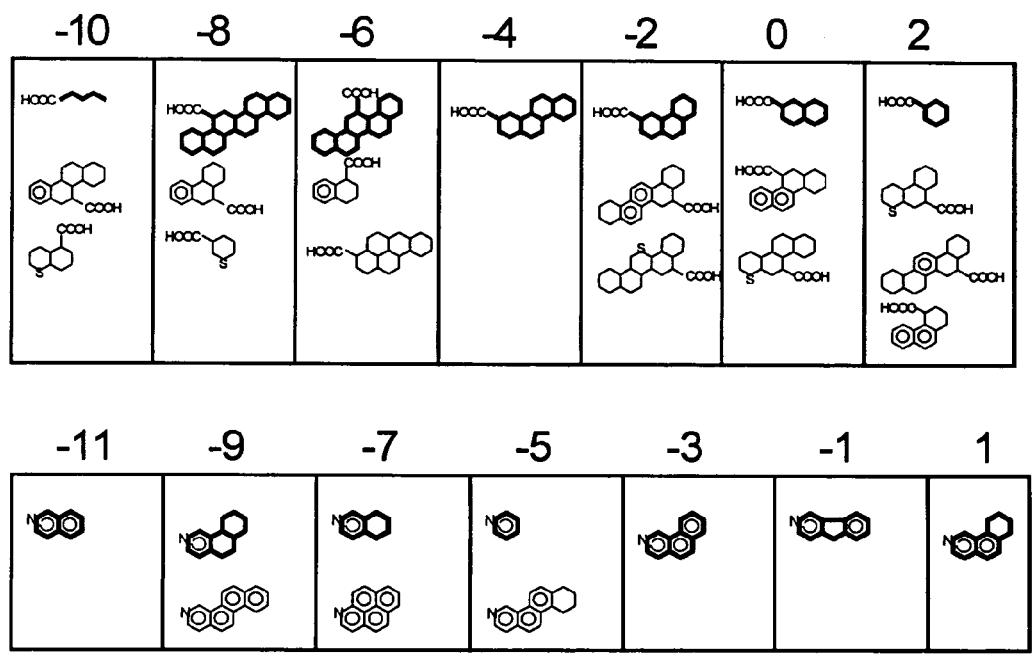
FIG. 14 shows the polar cores divided into even x-classes acids (−10, −8, −6, −4, −2, 0, 2) and odd x-class basic nitrogen.

Polar cores shown in FIG. 14 are organized into even X-class acids (−10, −8, −6, −4, −2, 0, 2), and odd X-class basic nitrogen molecules (−11, −9, −7, −5, −3, −1, 1). Some of the acid cores included in the model-of-composition contain aliphatic sulfur. Other polar oxygenates, e.g. alcohols and sulfoxides (not shown) are less abundant in petroleum than are acids, and do not appear in the model-of-composition. All odd x-class cores contain one basic nitrogen group.

Olefins and Thiophenes

Figure 15:
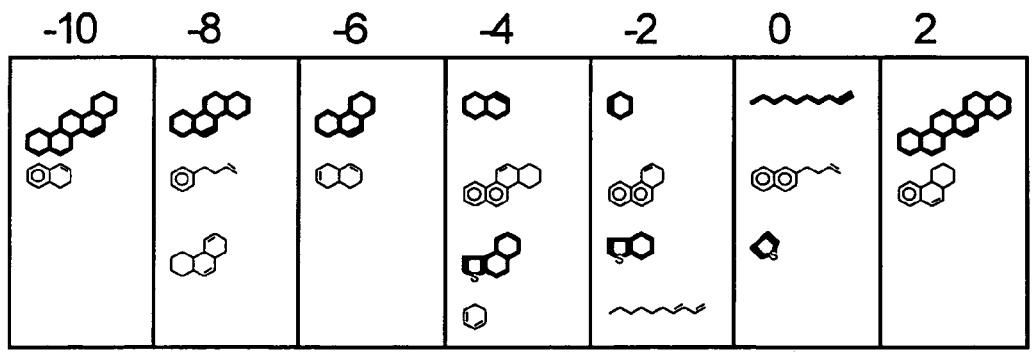
FIG. 15 shows olefin and thiophene cores that have x-classes that take even integers −10, −8, −6, −4, −2, 0, 2.

Olefin and thiophene cores shown in FIG. 15 have x-classes that take the even integers −10, −8, −6, −4, −2, 0, 2. Olefin and thiophene cores appear in FIG. 15; preferred structures are in bold. We have added a double bond to each of the preferred saturate cores (see bold structures of FIG. 8) to create the olefin cores in the top row of FIG. 15. The formation of each double bond present in an olefin requires the removal of two hydrogen atoms. Thus, the X-class of each of these mono-olefin cores is two less than that of the corresponding saturates core. Similarly, we have removed two hydrogen atoms from each of selected 1 ring aromatic cores (see FIG. 9), and from 2 ring aromatic cores (see FIG. 10), to create the olefin cores appearing in the second and third row of FIG. 10, respectively. Thiophenes (see fourth row of FIG. 15) are created by removing four hydrogen atoms from tetrahydrothiophene cores (see top row of FIG. 13). Olefin cores containing more than one double bond, e.g. diolefins, are not preferred in the model-of-composition (see bottom row of FIG. 15). Such molecules tend to be highly reactive and are therefore rare in petroleum.

3. Reconciling Analytical Measurements to the Model-of-Composition

The final step of Micro-Hydrocarbon Analysis is to reconcile analytical measurements to the model-of-composition. In particular, the model-of-composition must reproduce all measurements in the analytical protocol as closely as possible, and at the same time satisfy a set of property balances, e.g. mass and elemental composition.

One embodiment of this reconciliation procedure is to treat it as a constrained optimization problem: we optimize the model-of-composition's fidelity to the test results of the analytical protocol subject to the property balance constraints. Another embodiment of the reconciliation procedure is successive substitution, an iterative procedure in which the model-of-composition is adjusted to match the results of the analytical protocol in a prescribed sequence until changes in the model-of-composition between iterations fall below a prescribed tolerance.

a) Reconciliation by Constrained Optimization.

In the constrained optimization embodiment, we start with a model-of-composition whose reference molecular lump weight percents $\{w_i^*\}$ exactly the results of the Micro-Hydrocarbon Analysis protocol. Next, we seek a new set of weight percents $\{w_i\}$ that are minimally different from those of the reference, yet satisfy the property balances described above. To find these weight percents, we minimize the Lagrangian L (see e.g. Ref. [1]), defined by:

$$L \equiv \sum_{i=1}^{N} w_i^* \ln(w_i / w_i^*) + \sum_{j=1}^{NP} \lambda_j \left( b_j - \sum_{i=1}^{N} a_{ji} w_j \right) \quad (1)$$

The first term in Equation (1) is the Shannon information entropy content of the model-of-composition's weight percents $\{w_i\}$ relative to that of the reference weight percents $\{w_i^*\}$ (see e.g. Ref. [2]). The measured value of the property in the j-th balance is $b_j$. The density of property j in molecular lump i is $a_{ji}$. These property densities are either computed directly from each lump's molecular structure, or are correlated to measurements conducted on samples of known composition. $\lambda_j$ is the Lagrangian multiplier of the j-th property balance constraint. NP is the total number of property balances considered in reconciliation. N is the number of molecular lumps in the model of composition. The Lagrangian L is minimized when the following stationary conditions are satisfied:

$$\frac{\delta L}{\delta w} = 0, \frac{\partial L}{\partial \lambda_j} = 0 \quad (2)$$

$$\text{for } j = 1, \ldots, NP$$

From $\partial L/\partial \lambda_j = 0$ we recover the property balance equations $$b_j = \sum_{i=1}^{N} a_{ji} w_j.$$

We evaluate the functional derivative $\delta L/\delta w$ using calculus of variations (see e.g. [3]). For the Lagrangian in Equation (3), the stationary solution is $$w_i = w_i^* \exp\left(-1 + \sum_{j=1}^{NP} a_{ij} \lambda_j\right) \quad (3)$$

for $i = 1, \ldots, N$

Next, we substitute the stationary solution (4) into the property balance equations and eliminate the unknown weight percents $\{w_i\}$:

$$\sum_{i=1}^{N} a_{ji} w_i^* \exp\left(-1 + \sum_{k=1}^{NP} \lambda_k a_{ki}\right) = b_j \quad (4)$$

for $j = 1, \ldots, NP$

We solve the nonlinear algebraic equations (4) on a digital computer for the Lagrangian multipliers $\{\lambda_k\}$ using Newton's method. Once we have solved the equation system (4) for these Lagrangian multipliers, we substitute them into the stationary solution (3) and obtain the weight percents of the reconciled model-of-composition $\{W_i\}$.

b) Reconciliation by Successive Substitution

As in the constrained optimization reconciliation method described above, this embodiment of the reconciliation procedure also starts with model-of-composition whose reference molecular lump weight percents $\{w_i^*\}$ exactly the results of the Micro-Hydrocarbon Analysis protocol. Adjustments to the weight percents $\{w_i^*\}$ are done in sequence, i.e. the reconciled weight percents $\{w_i\}$ computed from the j-th property balance become the reference weight percents $\{W_i^*\}$ of the j+1-th property balance. Below we describe weight percent adjustment formulae for a scalar and distributed property targets, and the successive substitution reconciliation algorithm.

a) Scalar Property Targets

Scalar properties take a single number for the entire sample.

Simple Ratio Properties

A simple ratio property is linear in weight percents, its property density $a_{ji}$ is nonzero for selected molecules, and equals zero for others. Examples of simple ratio properties include elemental composition. For simple ratio properties, we combine the property balance with a total mass balance to obtain:

$$w_i = w_i^* \frac{b_j}{\sum_{k=1}^{N} a_{jk} w_k} \quad (5)$$

for $a_{ji} > 0$

Once we have adjusted (ratioed) the weight percents of molecules that possess the simple ratio property j, we adjust the weights of the molecules that do not possess this property:

$$w_i = w_i^* \frac{100 - \sum_{a_{jk}>0} w_k}{\sum_{a_{jk}=0} w_k^*} \quad (6)$$

for $a_{ji} = 0$

Averaged Properties

Averaged properties are scalar properties whose property densities $a_{ji} \neq 0$ for all molecular lumps $i=1, \ldots, N$. Examples of such averaged properties include API gravity, hydrogen content, octane number, and pour point. For averaged properties, the ratio method summarized in Equations 5 and 6 will not work. Instead, we have developed a factor $\phi$ that is a continuous function of the averaged property j whose target value equals $b_j$. This factor adjusts upward the weights of molecules whose property density $a_{ji}$ is less than that of the target $b_j$, and it adjusts downward the weights of molecules whose property density $a_{ji}$ is greater than the target value $b_j$. The net result is to shift the distribution of weights $\{w_i\}$ toward a distribution that satisfies the property constraint equation $$\sum_{i=1}^{N} a_{ji} w_i = b_j.$$

The continuous factor $\phi$ takes a cubic polynomial in the property value b:

$$\phi(b) = A_1 b^3 + A_2 b^2 + A_3 b + A_4 \quad (7)$$

We determine the four constants $A_1$ through $A_4$ with the following constraints:

Conservation of total weight:

$$100 = \sum_{i=1}^{N} w_i \phi \quad (8a)$$

Averaged property constraint:

$$b_j = \sum_{i=1}^{N} a_{ji} w_i \phi \quad (8b)$$

Smoothness at extreme values of the property j:

$$0 = \frac{\partial \phi}{\partial b} \text{ at } b = b_{\min,j} \quad (8c)$$

$$0 = \frac{\partial \phi}{\partial b} \text{ at } b = b_{\max,j} \quad (8d)$$

After we impose the constraints (8a-d) upon the factor $\phi_j$ defined in Equation 7, the factors and adjusted weights $\{w_i\}$ are computed as follows:

$$\phi = 1 + \gamma \Delta b_i \quad (9)$$

$$\gamma = \frac{b_j - \sum_{i=1}^{N} w_i * a_{ji}}{\sum_{i=1}^{N} a_{ji} w_i * \Delta b_i} \quad (10)$$

$$\Delta b_i = \left( a_{ji}^3 - \frac{\sum_{i=1}^{N} a_{ji}^3 w_i^*}{\sum_{i=1}^{N} w_i^*} \right) - \frac{3(b_{min,j} + b_{max,j})}{2} \left( a_{ji}^2 - \frac{\sum_{i=1}^{N} a_{ji}^2 w_i^*}{\sum_{i=1}^{N} w_i^*} \right) + 3(b_{min,j} + b_{max,j}) \left( a_{ji} - \frac{\sum_{i=1}^{N} a_{ji} w_i^*}{\sum_{i=1}^{N} w_i^*} \right) \quad (11)$$

$$w_i = w_i^* (1 + \gamma \Delta b_i) \text{ for } i = 1, \ldots, N \quad (12)$$

We avoid the occurrence of $\phi<0$ by restricting the property target range ($b_{min,j}, b_{max,j}$). If the actual target $b_j$ is outside this range, we approach this target in multiple steps.

In the case of multiple average property targets, we may calculate separate weight factors $\phi_j$ for each target property j. However, we have achieved much greater effectiveness by using a single factor that includes the dependence of all averaged property targets. The factor adds all cubic polynomials together in Equation 7, with three additional parameters for each target. Constraints in Equation 8 are also used for each property. Final factors and weight adjustments are similar in form to Equations 9-12.

b) Distributed Property Targets

In general, a distributed property target occurs when the property to be matched varies with some independent variable. The distribution of weight distilled with boiling point temperature, i.e. the distillation curve, is the most frequently encountered distributed target. In the successive substitution method, we design a factor $\phi$ that effectively "redistills" the reference weight distribution $\{w_i^*\}$ during each iteration of the reconciliation algorithm we describe below.

Figure 16A:
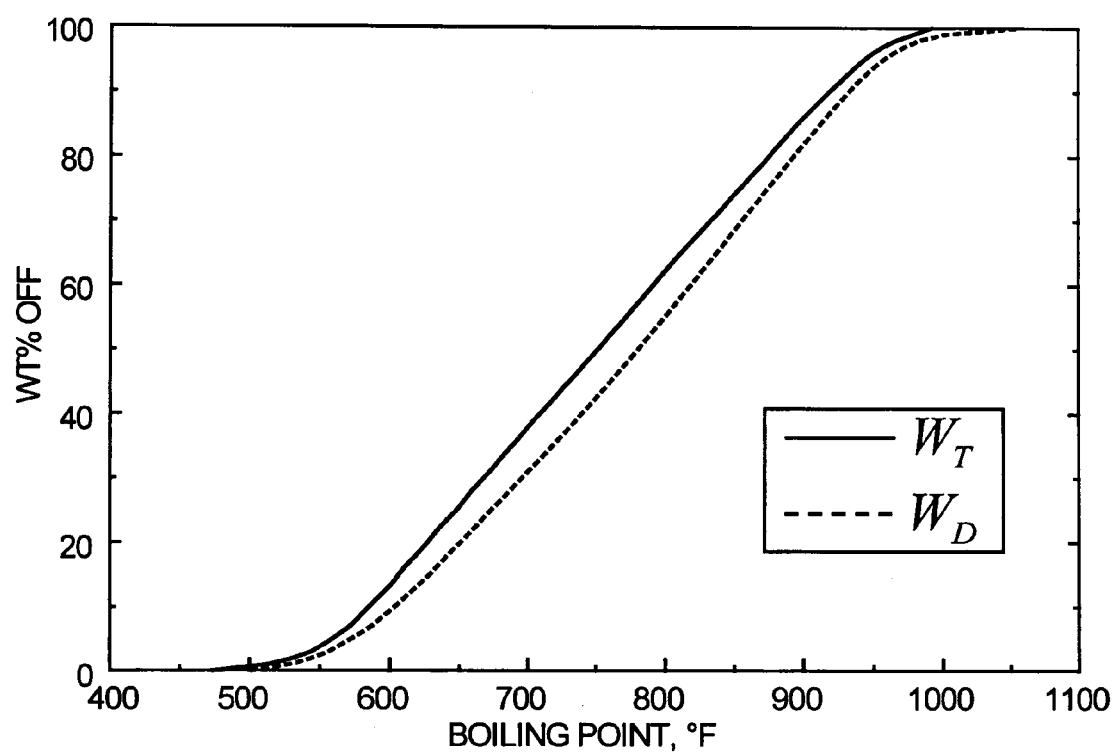
FIG. 16a shows the cumulative weight percent distilled off as a function of boiling point.
Figure 16B:
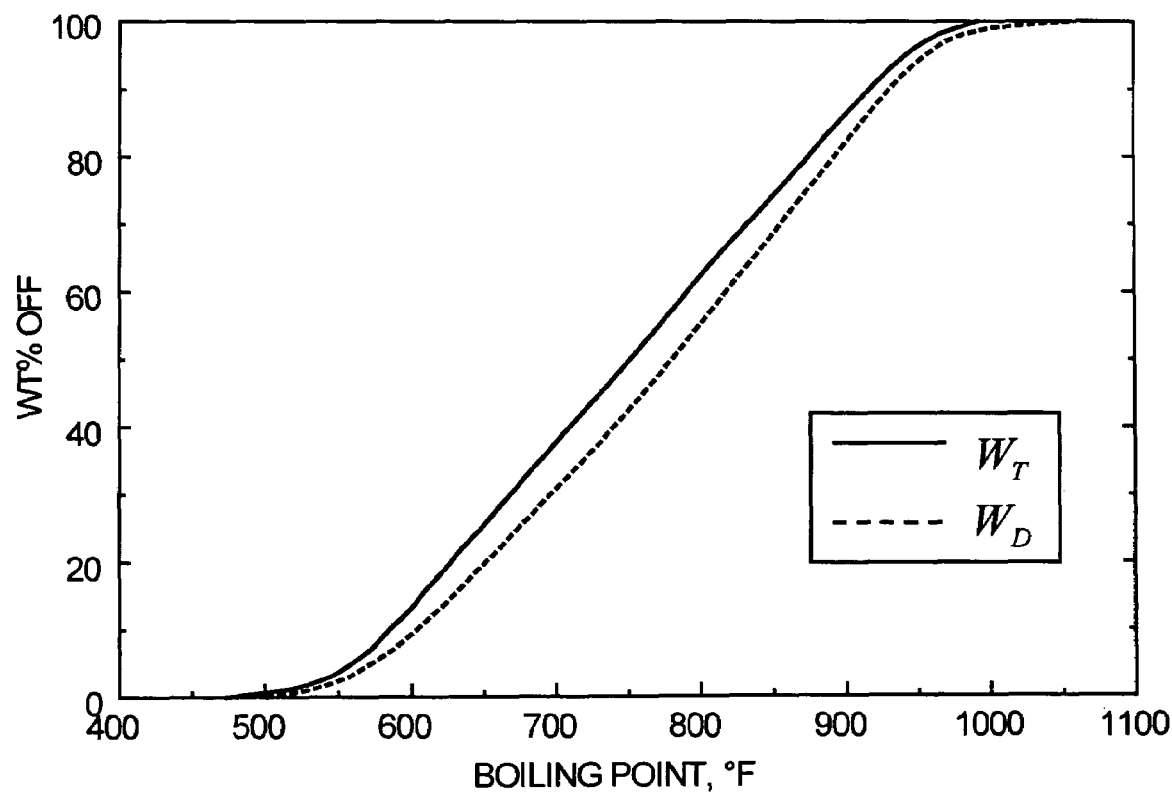
FIG. 16b shows the cumulative target distribution versus calculated distribution as a function of boiling point.
Figure 16C:
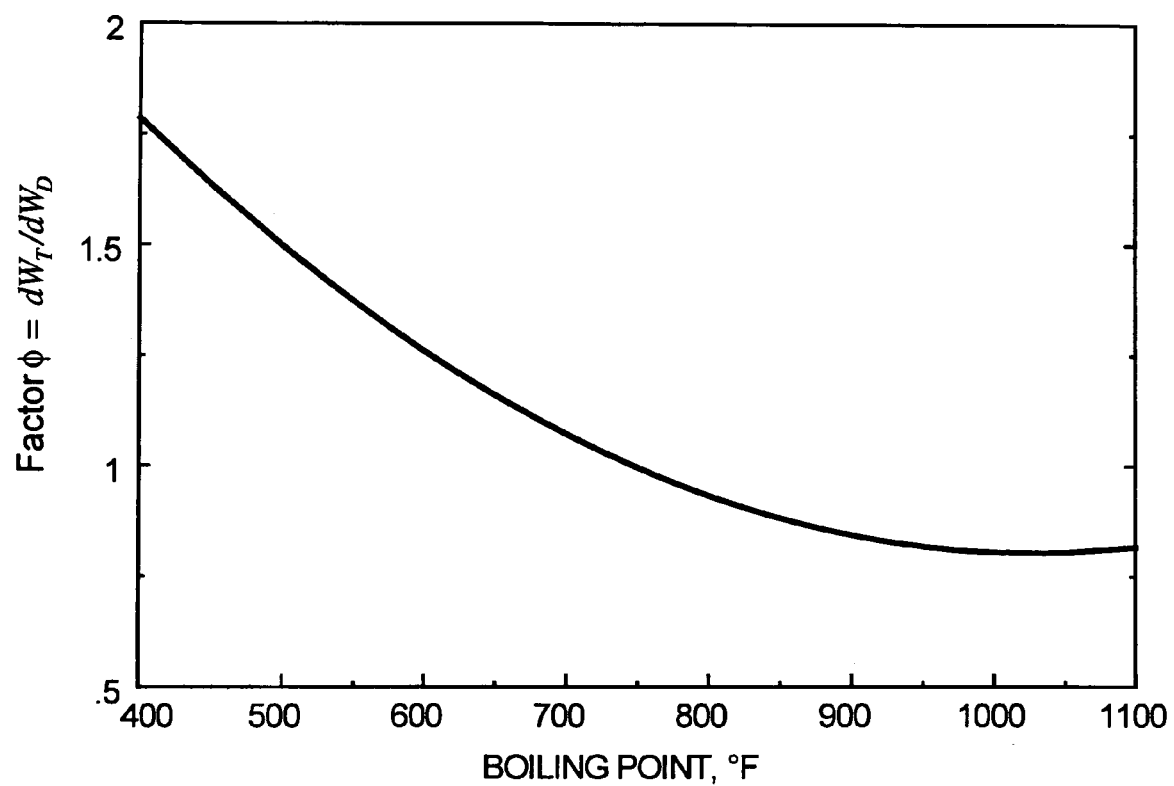
FIG. 16c shows $$\phi = \frac{dw_T}{dw_D}$$

Let W(BP) represent the cumulative weight percent distilled off at boiling point BP. The measured target distribution is $W_T$, and $W_D$ is calculated from the reference weight distribution $\{w_i^*\}$ of the molecular lumps. Both of these cumulative weight distributions are monotonically increasing functions of the boiling point BP (see FIG. 16a). In practice, the cumulative weight distribution $W_T$ is measured at discrete boiling points. Also, we calculate the distribution $W_D$ at the boiling points of each molecular lump. However, we may interpolate between these discrete boiling points using smooth functions that preserve the monotonically increasing nature of a cumulative weight distribution. After this interpolation, we determine the target distribution $W_T$ as a function of the calculated distribution $W_D$ at the same distillation boiling points (see FIG. 16b). Finally, we calculate the factor $\phi \equiv dW_T/dW_D$ as a function of boiling point (see FIG. 16c). We use the factor $\phi$ to adjust the reference weights as follows:

$$w_i = \frac{100 w_i * \phi(BP_i)}{\sum_{j=1}^{N} w_j * \phi(BP_j)} \text{ for } i = 1, \ldots, N \quad (13)$$

where $BP_i$ is the boiling point of molecular lump i.

c) The Successive Substitution Reconciliation Algorithm

In FIG. 17, we show the typical embodiment of the successive substitution reconciliation where a reference model-of-composition is adjusted to match one distributed target (boiling point), and more than one scalar property targets. In general, adjusting weight percents to match each target in sequence disrupts the previous match so that the weight percent adjustments are relaxed, or dampened, to ensure convergence of the successive substitution algorithm.

REFERENCES

1. Denn, M. M. "Optimization by Variational Methods", Chapter 1, McGraw-Hill, NYC, 1969.
2. Cover, T. M. and J. A. Thomas, "Elements of Information Theory", p. 18. J. Wiley & Sons, 1991.
3. Davis, H. T., "Statistical Mechanics of Phases, Interphases and Thin Films", Chapter 12, VCH Publishers, 1996.

What is claimed is:

1. A method to determine the model-of-composition of a petroleum or hydrocarbon sample from a small sample of said petroleum or hydrocarbon sample comprising
    a) obtaining measurements by analyzing the whole small sample absent separation into fractions with a combination of chromatograph and mass spectromer,
    b) quantifying output from step a) by applying response factors and normalizing petroleum or hydrocarbon classes to that measured by super critical fluid chromatography or other chromatographic techniques,
    c) reconciling the output from step b) with other analytical measurements that determine hydrocarbon and petroleum properties to obtain a model-of-composition of the petroleum or hydrocarbon sample.

2. The method of claim 1 wherein said chromatograph is a gas chromatograph.

3. The method of claim 1 wherein mass spectrometer is a high resolution mass spectrometer, such as time-of-flight spectrometer.

4. The method of claim 3 wherein input to the mass spectrometer is achieved by soft ionization.

5. The method of claim 4 wherein said soft ionization is field ionization.

6. The method of claim 1 wherein said other analytical measurements include supercritical fluid chromatography.

7. The method of claim 6 further comprising the step of generating petroleum or hydrocarbon lumps by supercritical fluid chromatography.

8. The method of claim 1 wherein said other analytical measurements include S-Sim Dist, Sim Dist, $^1$H-NMR, PIONA, GC-FID, sulfur and nitrogen contents.

9. The method of claim 1 wherein said other analytical measurement is S-Sim Dist.

10. The method of claim 1 wherein said other analytical measurement is Sim Dist.

11. The method of claim 1 wherein said other analytical measurement is $^1$H-NMR.

12. The method of claim 1 wherein said other analytical measurement is PIONA.

13. The method of claim 1 wherein said other analytical measurement is GC-FID.

14. The method of claim 1 wherein said other analytical measurement is sulfur and nitrogen contents.

15. The method of claim 1 wherein said sample is less than 1 ml.

16. The method of claim 7 wherein said sample is less than 0.2 ml.

17. The method of claim 1 wherein said model of composition is organized initially into major groups.

18. The method of claim 17 wherein said major groups are paraffins, naphthenes, 1-4 Ring Aromatics, non-basic nitrogen molecules, basic nitrogen molecules, sulfides and acids.

19. The method of claim 17 wherein each major group is organized by homologous series.

20. The method of claim 1 wherein the reconciling of step c) is carried out so that the model of composition substantially reproduces the measurements of step a) and step b) while satisfying a set of property balances.

21. The method of claim 20 wherein reconciling is a constrained optimization problem.

22. The method of claim 20 wherein the model-of-composition is optimized to produce the measurements of claim 1, step a), and step b) subject to property balance constraints.

23. The method of claim 21 wherein reconciling is a successive substitution procedure.

24. The method of claim 21 wherein said successive substitution is an iterative procedure in which the model-of-composition matches the measurements of claim 1, step a), and step b), in a prescribed sequence until changes in the model-of-composition between iterations fall below a predetermined value.

* * * * *